US012318256B2

(12) United States Patent
Waechter-Stehle et al.

(10) Patent No.: US 12,318,256 B2
(45) Date of Patent: *Jun. 3, 2025

(54) 3D ULTRASOUND IMAGING SYSTEM

(71) Applicant: KONINKLIJKE PHILIPS N.V., Eindhoven (NL)

(72) Inventors: Irina Waechter-Stehle, Hamburg (DE); Juergen Weese, Norderstedt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 18/636,651

(22) Filed: Apr. 16, 2024

(65) Prior Publication Data

US 2024/0252150 A1 Aug. 1, 2024

Related U.S. Application Data

(63) Continuation of application No. 17/982,709, filed on Nov. 8, 2022, now Pat. No. 11,986,355, which is a
(Continued)

(51) Int. Cl.
*A61B 8/00* (2006.01)
*A61B 8/08* (2006.01)
(Continued)

(52) U.S. Cl.
CPC .............. *A61B 8/523* (2013.01); *A61B 8/085* (2013.01); *A61B 8/0883* (2013.01); *A61B 8/14* (2013.01);
(Continued)

(58) Field of Classification Search
CPC ............. A61B 8/12; A61B 8/14; A61B 8/463; A61B 8/483; G01S 15/8993; G06T 2207/10136; G06T 2207/30048
See application file for complete search history.

(56) References Cited

U.S. PATENT DOCUMENTS 5,315,512 A 5/1994 Roth
7,604,597 B2 10/2009 Murashita et al.
(Continued)

OTHER PUBLICATIONS

Ecabert, O. et al, "Automatic Model-based Segmentation of the Heart in CT Images" IEEE Transactions on Medical Imaging, vol. 27(9) p. 1189-1291 (2008).
(Continued)

*Primary Examiner* — Jason M Ip

(57) ABSTRACT

An ultrasound imaging system having an image processor configured to receive at volume data resulting from a three-dimensional ultrasound scan of a body and to provide corresponding display data, an anatomy detector configured to detect a position and orientation of an anatomical object of interest within the volume data, a slice generator for generating a plurality of two-dimensional slices from the volume data, wherein the slice generator is configured to define respective slice locations based on the results of the anatomy detector for the anatomical object of interest so as to obtain a set of two-dimensional standard views of the anatomical object of interest, wherein the slice generator is further configured to define for each two-dimensional standard view which anatomical features of the anatomical object of interest are expected to be contained. An evaluation unit evaluates a quality factor for each of the two-dimensional slices.

20 Claims, 7 Drawing Sheets

Related U.S. Application Data continuation of application No. 14/781,059, filed as application No. PCT/IB2014/060004 on Mar. 20, 2014, now Pat. No. 10,709,425.

(60) Provisional application No. 61/807,885, filed on Apr. 3, 2013.

(51) Int. Cl.
| | |
|---|---|
| *A61B 8/14* | (2006.01) |
| *G01S 15/89* | (2006.01) |
| *G06F 16/51* | (2019.01) |
| *G06F 18/22* | (2023.01) |
| *G06T 7/00* | (2017.01) |
| *G06T 7/10* | (2017.01) |
| *G06T 7/60* | (2017.01) |
| *G06T 7/70* | (2017.01) |
| *G06T 15/00* | (2011.01) |
| *G06V 10/42* | (2022.01) |
| *A61B 8/12* | (2006.01) |

(52) U.S. Cl.
CPC ............. *A61B 8/463* (2013.01); *A61B 8/483* (2013.01); *G01S 15/8993* (2013.01); *G06F 16/51* (2019.01); *G06F 18/22* (2023.01); *G06T 7/0014* (2013.01); *G06T 7/10* (2017.01); *G06T 7/60* (2013.01); *G06T 7/70* (2017.01); *G06T 15/005* (2013.01); *G06V 10/42* (2022.01); *A61B 8/12* (2013.01); *G06T 2207/10136* (2013.01); *G06T 2207/30048* (2013.01); *G06T 2207/30168* (2013.01)

(56) References Cited

U.S. PATENT DOCUMENTS

| | | |
|---|---|---|
| 8,290,225 B2 | 10/2012 | Lobregt et al. |
| 2004/0210138 A1 | 10/2004 | Murashita et al. |
| 2010/0195881 A1 | 8/2010 | Orderud et al. |
| 2011/0201935 A1 | 8/2011 | Collet-Billon et al. |
| 2012/0065510 A1 | 3/2012 | Snare et al. |
| 2012/0232394 A1 | 9/2012 | Toji |

OTHER PUBLICATIONS

Balzer et al, "Real-time Three-Dimensional Transoesophageal Echocardiography for Guidance of non-coronary Interventions in the Cather Laboratory" European Journal of Echocardiography (2009) 10, p. 341-419.

3D ULTRASOUND IMAGING SYSTEM

RELATED APPLICATIONS

This application is a continuation of U.S. patent application Ser. No. 17/982,709, filed on Nov. 8, 2022, which in turn is a continuation of U.S. patent application Ser. No. 14/781,059, filed on Sep. 29, 2015, which is the U.S. National Phase Application under 35 U.S.C. § 371 of International Application No. PCT/IB2014/060004, filed on Mar. 20, 2014, which claims the benefit of U.S. Provisional Application No. 61/807,885, filed on Apr. 3, 2013, the disclosure of which is hereby incorporated by reference herein.

FIELD OF THE INVENTION

The present invention relates to three-dimensional ultrasound imaging. In particular, the present invention relates to the generation and evaluation of two-dimensional standard views from three-dimensional ultrasonic volume data. An exemplary technical application of the present invention is the generation of two-dimensional transesophageal echocardiography (TEE) images based on one or more obtained three-dimensional TEE scans.

BACKGROUND OF THE INVENTION

A transesophageal echocardiogram is an alternative way to perform an echocardiogram. A specialized probe containing an ultrasound transducer at its tip is passed into the patient's esophagus. This allows to record precise ultrasound images of different components of the human heart.

For a full transesophageal echocardiography (TEE) examination 20 different 2D TEE views have to be acquired. These 2D TEE views are predefined views (e.g. ME four chamber, ME two chamber, TG basal SAX, . . . ), which are in practice also referred to as the 2D TEE standard views. In order to acquire these images, the sonographer has to reposition and reorient the ultrasound probe relative to the patient according to a very elaborated protocol for each of the 20 2D TEE standard views. This is a tedious and long procedure, which may take about 20 to 30 minutes.

The whole TEE procedure is quite uncomfortable for the patient. Apart from that, manually finding the above-mentioned standard views in order to allow a reliable diagnosis requires a relatively high level of skill of the sonographer (e.g. doctor). Moreover, this process is relatively error-prone.

US 2011/0201935 A1, a former patent application filed by the applicant, proposes for the similar field of fetal heart examinations the usage of 3D ultrasound scanning technology. The therein proposed ultrasound imaging system comprises an ultrasound scanning assembly that provides volume data resulting from a three-dimensional scan of a body. It further comprises a feature extractor that searches for a best match between the volume data and a geometrical model of an anatomical entity. The geometrical model comprises respective segments representing respective anatomic features. Accordingly, the feature extractor provides an anatomy-related description of the volume data, which identifies respective geometrical locations of respective anatomic features in the volume data. Standard views may therefore be automatically obtained from the volume data, which is of course less operator-dependent and allows a more reliable diagnosis. Compared to manually acquiring each 2D standard view separately, this is of major advantage.

However, there is still need for further improvement.

SUMMARY OF THE INVENTION

It is an object of the present invention to provide an improved ultrasound imaging system, which allows a quicker, more comfortable and more reliable analysis of an anatomical object, e.g. of the human heart. It is furthermore an object of the present invention to provide a corresponding method and a computer program for implementing such method.

In a first aspect of the present invention an ultrasound imaging system is presented that comprises:

an image processor configured to receive at least one set of volume data resulting from a three-dimensional ultrasound scan of a body and to provide corresponding display data, an anatomy detector configured to detect a position and orientation of an anatomical object of interest within the at least one set of volume, a slice generator for generating a plurality of two-dimensional slices from the at least one set of volume data, wherein said slice generator is configured to define respective slice locations based on the results of the anatomy detector for the anatomical object of interest so as to obtain a set of two-dimensional standard views of the anatomical object of interest, wherein the slice generator is further configured to define for each two-dimensional standard view which anatomical features of the anatomical object of interest are expected to be contained within said two-dimensional view, and an evaluation unit for evaluating a quality factor for each of the generated plurality of two-dimensional slices by comparing each of the slices with the anatomical features expected for the respective two-dimensional standard view.

In a further aspect of the present invention a method of generating and evaluating two-dimensional standard views from three-dimensional ultrasonic volume data is presented which comprises the steps of:

receiving at least one set of volume data resulting from a three-dimensional ultrasound scan of a body, detecting a position and orientation of an anatomical object of interest within the at least one set of volume data, generating a plurality of two-dimensional slices from the at least one set of volume data, by defining respective slice locations based on the detected position and orientation of the anatomical object of interest so as to obtain a set of two-dimensional standard views of the anatomical object of interest, defining for each two-dimensional standard view which anatomical features of the anatomical object of interest are expected to be contained, and evaluating a quality factor for each of the generated plurality of two-dimensional slices by comparing each of the slices with the anatomical features expected for the respective two-dimensional standard view.

In a still further aspect of the present invention a computer program is presented comprising program code means for causing a computer to carry out the steps of the above-mentioned method when said computer program is carried out on the computer.

In addition to the method disclosed in US 2011/0201935 A1 it is defined for each 2D standard view which anatomical features of the anatomical object of interest are expected to be contained. An evaluation unit may then evaluate a quality factor for each of the generated plurality of 2D slices by comparing each of the slices with the anatomical features expected for the respective 2D standard view.

In other words, for each generated two-dimensional slice (2D standard view) it is computed how good the 2D standard view is covered within the received set of 3D ultrasound volume data. Depending on the field of view of the performed 3D ultrasound scan it may, for example, be the case that a received set of 3D ultrasound volume data is useful to generate one or a plurality of 2D standard views, while it is less useful to generate other standard views.

Depending on the field of view a received 3D ultrasound volume data set may, for example, cover most or all parts of the left ventricle of the human heart, while it does not cover or only covers few parts of the right ventricle of the human heart. In this case the presented ultrasound imaging system would automatically identify that the received volume data set is only useful for the 2D standard views of the left ventricle, but less useful for the 2D standard views of the right ventricle.

The evaluated quality factor for each of the generated 2D slices may e.g. be a numerical value that results from the comparison of each of the generated slices with the anatomical features expected for the respective 2D standard view. For example, the coverage of a 2D standard view by the received set of 3D volume data may be determined by determining the overlap of the structures that should be covered (expected anatomical features) and the field of view of the performed 3D ultrasound scan.

According to an embodiment of the present invention, the anatomy detector is configured to conduct a model-based segmentation of the at least one set of volume data by finding a best match between the at least one set of volume data and a geometrical model of the anatomical object of interest in order to detect the position and orientation of the anatomical object of interest. The slice generator may be configured to define the respective slice locations of the anatomical object of interest based on said geometrical model.

In this case a geometrical mesh model of an anatomical object of interest (e.g. of the heart) may be used for a model-based segmentation of the 3D ultrasound image (also referred to as volume data). The plurality of 2D slices may be generated based on said geometrical mesh model so as to automatically obtain a set of 2D standard views of the anatomical object of interest.

In order to compute the 2D standard views based on the geometrical model, landmarks may be encoded in the model. These landmarks encoded in the geometrical model may be identified and mapped onto the 3D ultrasonic volume data. For example, a set of three or more landmarks can represent a plane that leads to or corresponds to a 2D standard view. For example to compute the four chamber view of the heart, this plane is given by the center of the mitral valve, the center of the tricuspid valve and the apex.

It shall be noted that, instead of using a model-based segmentation, the position and orientation of the anatomical object of interest may also be determined (directly) by identifying landmarks or specific anatomical features within the 3D ultrasound image.

According to a further embodiment of the present invention, the quality factor that is evaluated within the evaluation unit for each of the generated plurality of two-dimensional slices is a quantitative factor that includes a ratio to which extent the expected anatomical features are included in the respective two-dimensional slice.

According to a further refinement, the evaluation unit is configured to evaluate the quality factor for each of the generated plurality of two-dimensional slices by comparing a field of view of each of the two-dimensional slices to the geometrical model of the anatomical object.

According to a still further embodiment of the present invention, the ultrasound imaging system further comprises a display, wherein the image processor is configured to generate display data for simultaneously illustrating graphical representations of a plurality of two-dimensional slices corresponding to different standard views of the anatomical object of interest on the display.

In other words, the generated 2D slices may be simultaneously presented on the display. This allows a doctor an easy comparison of the different standard views.

Preferably, the image processor is furthermore configured to generate display data for illustrating a graphical representation of the quality factor for each of the two-dimensional slices on the display. The graphical representation of the quality factor preferably comprises an icon and/or a percentage. The quality factor may, for example, be presented as a traffic light to the user. In this case a green light e.g. shows a good/sufficient coverage of the respective 2D standard view by the 2D slice generated from the 3D ultrasound volume data. A yellow light e.g. shows a coverage of the respective 2D standard view by the generated 2D slice that could still be sufficient. And a red light e.g. indicates that the field of view of the generated 2D slice does not cover enough anatomical features that should be included in the respective 2D standard view. In this case the user receives a very easy indication about the quality of the computed 2D slices.

According to an embodiment of the present invention, the ultrasound imaging system further comprises:
a memory for storing a plurality of sets of volume data resulting from a plurality of different three-dimensional scans of a body and for storing the plurality of two-dimensional slices generated from the plurality of sets of volume data and their quality factors; and
a selector for selecting for each two-dimensional standard view a two-dimensional slice having the highest quality factor by comparing the evaluated quality factors of corresponding two-dimensional slices generated from each of the plurality of sets of volume data.

This embodiment leads to a further significant improvement. It allows to compare 2D slices with each other that correspond to the same 2D standard views but were generated from different 3D ultrasound scans (different sets of volume data). The different 3D ultrasound scans may e.g. result from scans at different positions or orientations of the ultrasound probe. The ultrasound imaging system may, for example, comprise an initialization unit that initializes the acquisition of a 3D ultrasound scan and the above-mentioned subsequent procedure of generating the 2D slices therefrom each time the position or orientation of the ultrasound probe is changed.

In this case several sets of volume data and 2D slices generated therefrom may be stored within a memory. The selector may then select for each of the 2D standard views the 2D slice having the highest quality factor. This means that if more than one 3D ultrasound scan is performed, the system itself automatically selects the best version out of all generated 2D slices for each 2D standard view. Only these best versions may then be illustrated on the display for each 2D standard view. Thus, only the best examples are illustrated to the user. In combination with the above-mentioned representation of the quality factor on the display (e.g. using an icon such as a traffic light), the user therefore receives a direct feedback, whether all standard views are covered by the combination of all performed 3D ultrasound scans, or whether he/she has to acquire a further set of 3D volume data by performing an additional ultrasound scan.

However, it has been shown that a lot less scans have to be performed in contrast to manually acquiring the 2D standard views with a 2D ultrasound scanner. Two or three 3D ultrasound scans of the human heart may, for example, already be enough in order to generate all 20 2D TEE standard views. Since the system itself selects the best generated 2D slice for each 2D standard view, the operation of the presented system is fairly easy. The user so to say only has to acquire enough 3D ultrasound scans until a "green light" is received for each standard view. This may even be done by the user in a trial and error manner without having to follow the usual elaborated protocols for acquiring the predefined standard views.

Even though in the foregoing paragraphs it has been mainly focused on the generation of transesophageal echocardiography (TEE), it shall be pointed out that the presented ultrasound imaging system may also be used for generating and evaluating 2D standard views of other organs or other anatomical objects of humans and/or animals. It could be used in a similar way e.g. for an analysis of the liver or an unborn baby (fetal ultrasound).

In the foregoing it has mainly been focused on the image processing part of the presented ultrasound imaging system. According to a further embodiment, the ultrasound imaging system may further include:

a transducer array configured to provide an ultrasound receive signal, a beam former configured to control the transducer array to perform the three-dimensional scan of the body, and further configured to receive the ultrasound receive signal and to provide an image signal, a controller for controlling the beam former, and a signal processor configured to receive the image signal and to provide the three-dimensional volume data.

According to a further preferred embodiment, said controller may be configured to control the beam former to control the transducer array to perform an additional two-dimensional scan for a two-dimensional standard view of the anatomical object of interest if the quality factor of one of the plurality of two-dimensional slices generated by the slice generator is above a predetermined threshold.

In other words, this means that the ultrasound imaging system is configured to automatically perform an additional 2D ultrasound scan if it is found in the above-mentioned analysis that one of the slices generated from the 3D ultrasound volume data covers the respective 2D standard view in a sufficiently good manner. The system would then recognize that the acquired field of view at the position and orientation of the ultrasound probe is meaningful for acquiring the 2D standard view in a direct manner (by an extra 2D ultrasound scan at this position and orientation). This additional 2D scan would then be taken in the further image processing as 2D standard view instead of generating said 2D standard view by an interpolation from the 3D volume data as mentioned above. In this case the local image resolution may even be increased for said standard view.

It shall be understood that the claimed method has similar and/or identical preferred embodiments as the claimed ultrasound imaging system, as defined above and as defined in the dependent claims.

According to an embodiment, the position and orientation of the anatomical object of interest are detected by conducting a model-based segmentation of the at least one set of volume data and finding a best match between the at least one set of volume data and a geometrical model of the anatomical object of interest, and wherein the respective slice locations are defined based on said geometrical model.

According to a further embodiment, the claimed method comprises the steps of:

receiving and storing a plurality of sets of volume data resulting from a plurality of three-dimensional scans of a body, generating and storing a plurality of different two-dimensional slices generated from each of the plurality of sets of volume data together with their quality factors; and selecting for each two-dimensional standard view a two-dimensional slice having the highest quality factor by comparing the evaluated quality factors of corresponding two-dimensional slices generated from each of the plurality of sets of volume data.

According to a further embodiment, the claimed method comprises the steps of simultaneously illustrating graphical representations of a plurality of two-dimensional slices corresponding to different standard views of the anatomical object of interest on a display.

According to a further embodiment, the claimed method comprises the step of illustrating a graphical representation of the quality factor for each of the two-dimensional slices on a display.

According to a still further embodiment, the claimed method comprises the step of performing an additional two-dimensional scan for a two-dimensional standard view of the anatomical object of interest if the quality factor of one of the generated plurality of two-dimensional slices is above a predetermined threshold.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
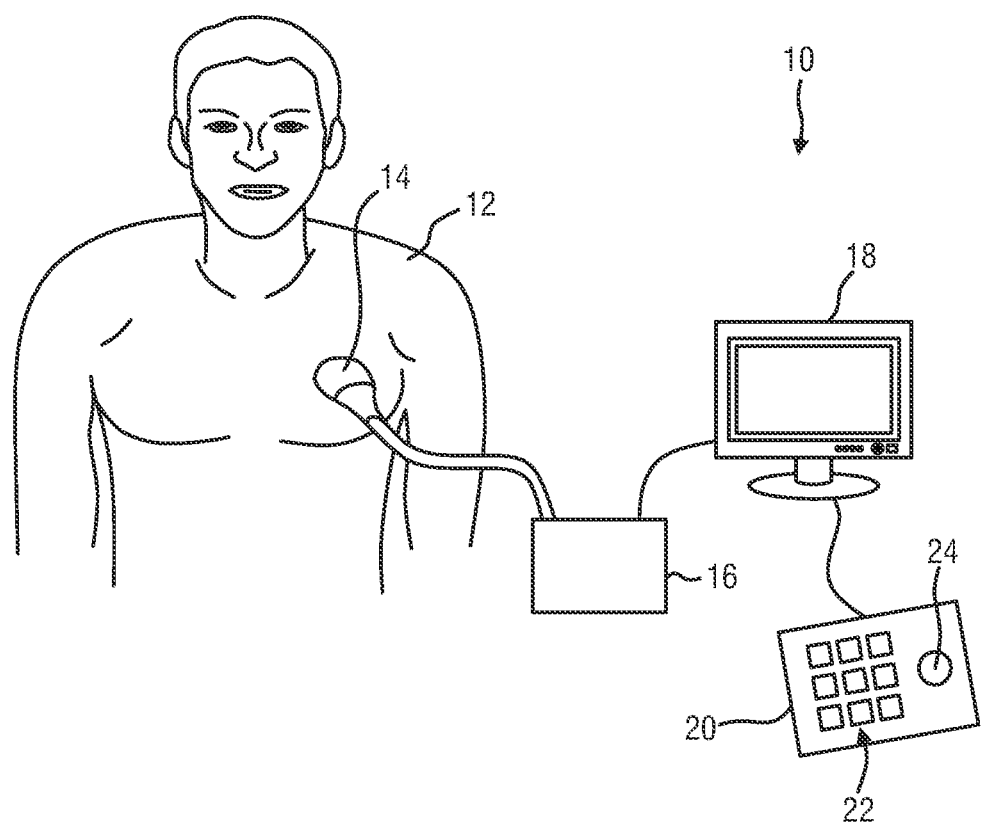
FIG. 1 shows a schematic representation of an ultrasound imaging system in use to scan a volume of a patient's body.

FIG. 1 shows a schematic illustration of an ultrasound system 10 according to an embodiment, in particular a medical three-dimensional (3D) ultrasound imaging system. The ultrasound imaging system 10 is applied to inspect a volume of an anatomical site, in particular an anatomical site of a patient 12. The ultrasound system comprises an ultrasound probe 14 having at least one transducer array having a multitude of transducer elements for transmitting and/or receiving ultrasound waves. In one example, the transducer elements each can transmit ultrasound waves in form of at least one transmit impulse of a specific pulse duration, in particular a plurality of subsequent transmit pulses. The transducer elements are preferably arranged in a two-dimensional array, in particular for providing a multi-planar or three-dimensional image.

A particular example for a three-dimensional ultrasound system which may be applied for the current invention is the CX40 Compact Xtreme ultrasound system sold by the applicant, in particular together with a X6-1 or X7-2t TEE transducer of the applicant or another transducer using the xMatrix technology of the applicant. In general, matrix transducer systems as found on Philips iE33 systems or mechanical 3D/4D transducer technology as found, for example, on the Philips iU22 and HD15 systems may be applied for the current invention.

A 3D ultrasound scan typically involves emitting ultrasound waves that illuminate a particular volume within a body, which may be designated as target volume. This can be achieved by emitting ultrasound waves at multiple different angles. A set of volume data is then obtained by receiving and processing reflected waves. The set of volume data is a representation of the target volume within the body.

It shall be understood that the ultrasound probe 14 may either be used in a non-invasive manner (as shown in FIG. 1) or in an invasive manner as this is usually done in TEE (not explicitly shown). The ultrasound probe 14 may be hand-held by the user of the system, for example medical staff or a doctor. The ultrasound probe 14 is applied to the body of the patient 12 so that an image of an anatomical site, in particular an anatomical object of the patient 12 is provided.

Further, the ultrasound system 10 may comprise a controlling unit 16 that controls the provision of a 3D image via the ultrasound system 10. As will be explained in further detail below, the controlling unit 16 controls not only the acquisition of data via the transducer array of the ultrasound probe 14, but also signal and image processing that form the 3D images out of the echoes of the ultrasound beams received by the transducer array of the ultrasound probe 14.

The ultrasound system 10 may further comprise a display 18 for displaying the 3D images to the user. Still further, an input device 20 may be provided that may comprise keys or a keyboard 22 and further inputting devices, for example a trackball 24. The input device 20 might be connected to the display 18 or directly to the controlling unit 16.

Figure 2:
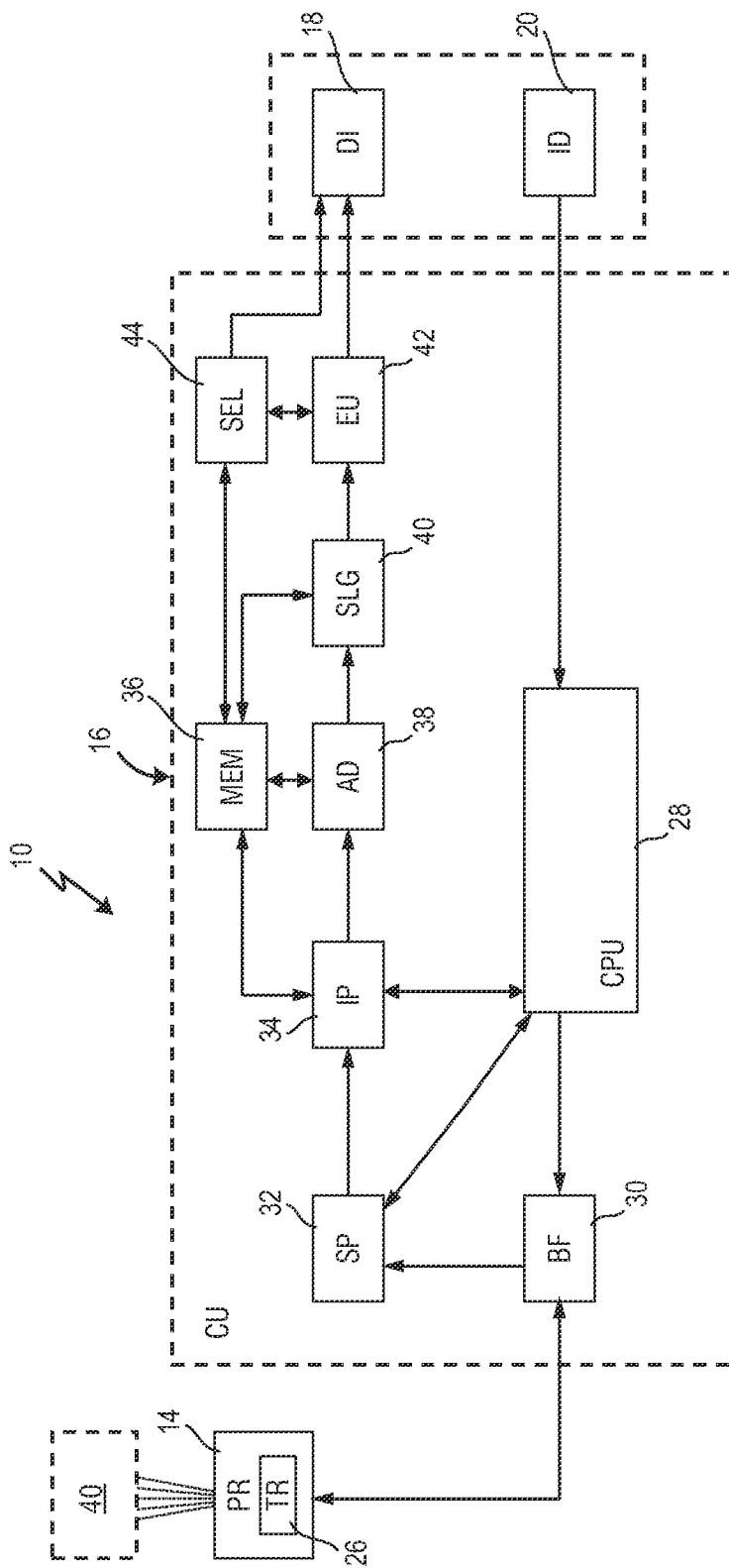
FIG. 2 shows a schematic block diagram of an embodiment of the ultrasound imaging system.

FIG. 2 shows a schematic block diagram of the ultrasound system 10. As already laid out above, the ultrasound system 10 comprises an ultrasound probe (PR) 14, the controlling unit (CU) 16, the display (DI) 18 and the input device (ID) 20. As further laid out above, the probe (PR) 14 comprises a phased two-dimensional transducer array (TR) 26. In general, the controlling unit (CU) 16 may comprise a central processing unit (CPU) 28 that may include analog and/or digital electronic circuits, a processor, microprocessor or the like to coordinate the whole image acquisition and provision. However, it has to be understood that the central processing unit (CPU) 28 does not need to be a separate entity or unit within the ultrasound system 10. It can be a part of the controlling unit 16 and generally be hardware or software implemented. The current distinction is made for illustrative purposes only. The central processing unit (CPU) 28 as a part of the controlling unit (CU) 16 may control a beam former (BF) 30 and, by this, what images of the volume 40 are taken and how these images are taken. The beam former (BF) 30 generates the voltages that drive the transducer array (TR) 26, determines repetition frequencies, it may scan, focus and apodize the transmitted beam and the reception of receive beam(s) and may further amplify filter and digitize the echo voltage stream returned by the transducer array (TR) 26. Further, the central processing unit (CPU) 28 of the controlling unit (CU) 16 may determine general scanning strategies. Such general strategies may include a desired volume acquisition rate, lateral extent of the volume, an elevation extent of the volume, maximum and minimum line densities and scanning line times. The beam former (BF) 30 further receives the ultrasound signals from the transducer array (TR) 26 and forwards them as image signals.

Further, the ultrasound system 10 comprises a signal processor (SP) 32 that receives the image signals. The signal processor (SP) 32 is generally provided for analog-to-digital-converting, digital filtering, for example, bandpass filtering, as well as the detection and compression, for example a dynamic range reduction, of the received ultrasound echoes or image signals. The signal processor 32 forwards image data.

Further, the ultrasound system 10 comprises an image processor (IP) 34 that converts image data received from the signal processor 32 into display data. In particular, the image processor 34 receives the image data, preprocesses the image data and may store it in a memory (MEM) 36. This image data is then further post-processed to provide images to the user via the display 18. In the current case, in particular, the image processor 34 may form the three-dimensional images out of a multitude of two-dimensional images.

The ultrasound system 10 may in the current case further comprise an anatomy detector (AD) 38, a slice generator (SLG) 40 and an evaluation unit (EU) 42. It shall be noted that the latter mentioned components may either be realized as separate entities, but may also be included in the image processor 34. All these components may be hardware and/or software implemented.

The anatomy detector (AD) 38 identifies the orientation and position of the anatomical object of interest within the acquired 3D volume data. The anatomy detector (AD) may thereto be configured to conduct a model-based segmentation of the acquired 3D volume data. This may be done by finding a best match between the at least one set of volume data and a geometrical mesh model of the anatomical object of interest. The model-based segmentation may, for example, be conducted in a similar manner as this is described for a model-based segmentation of CT images in Ecabert, O. et al.: "Automatic Model-based Segmentation of the Heart in CT Images", IEEE Transactions on Medical Imaging, Vol. 27(9), p. 1189-1291, 2008. The geometrical mesh model of the anatomical object of interest may comprise respective segments representing respective anatomic features. Accordingly, the anatomy detector 38 may provide an anatomy-related description of the volume data, which identifies respective geometrical locations of respective anatomic features in the volume data.

Such a model-based segmentation usually starts with the identification of the orientation of the anatomical object of interest (e.g. the heart) within the 3D ultrasonic volume data. This may, for example, be done using a three-dimensional implementation of the Generalized Hough Transform. Pose misalignment may be corrected by matching the geometrical model to the image making use of a global similarity transformation. The segmentation comprises an initial model that roughly represents the shape of the anatomical object of interest. Said model may be a multi-compartment mesh model. This initial model will be deformed by a transformation. This transformation is decomposed into two transformations of different kinds: A global transformation that can translate, rotate or rescale the initial shape of the geometrical model, if needed, and a local deformation that will actually deform the geometrical model so that it matches more precisely to the anatomical object of interest. This is usually done by defining the normal vectors of the surface of the geometrical model to match the image gradient; that is to say, the segmentation will look in the received ultrasonic image for bright-to-dark edges (or dark-to-bright), which usually represent the tissue borders in ultrasound images, i.e. the boundaries of the anatomical object of interest.

The segmented 3D volume data may then be further post-processed. The slice generator (SLG) 40 generates a plurality of two-dimensional slices from the 3D volume data. Landmarks are thereto encoded within the geometrical model that defines the planes of said 2D slices. A set of three or more landmarks can represent a plane. These encoded landmarks may be mapped onto the segmented 3D volume data so as to obtain a set of 2D standard views of the anatomical object of interest generated from the 3D volume data. The slice generator 40 may be furthermore configured to define for each 2D standard view which anatomical features of the anatomical object of interest are expected to be contained within said view. This may be done using the geometrical model that is encoded with the anatomic features of the anatomical object of interest. It should thus be known which anatomical features should occur in which 2D standard view.

The evaluation unit (EU) 42 may then evaluate a quality factor for each of the generated plurality of 2D slices by comparing each of said generated slices with the anatomical features expected for the respective 2D standard view. In other words, the evaluation unit 42 computes the coverage of each of the 2D standard views by the 3D volume data. This may be done by computing the overlap of the structure that should be covered and the field of view of the 3D ultrasound scan. The quality factor that is evaluated within the evaluation unit 42 for each of the generated plurality of 2D slices may thus be a quantitative factor that includes a ratio to which extent the expected anatomical features are included in the respective 2D slice. This may be done by comparing the field of view of each of the 2D slices to the geometrical model of the anatomical object.

In still other words, this means that for each 2D slice that is generated from the received 3D ultrasound volume data, it is determined how good the 2D standard view, that corresponds to the generated 2D slice, is covered. This information can be presented as a graphical icon, e.g. as a traffic light, and/or as a percentage on the display 18.

As it will be explained further below in detail with reference to FIGS. 5 to 7, the generated 2D slices of the anatomical object of interest are preferably illustrated on the display 18 simultaneously, wherein each illustrated 2D slice is illustrated together with a graphical representation of the quality factor (icon and/or percentage) that indicates the quality of the respective 2D slice.

In practice there is usually not only performed a single 3D ultrasound scan of the anatomical object of interest. Preferably, a plurality of 3D ultrasound scans of the anatomical object of interest are performed. This results in a plurality of sets of volume data, which result from the plurality of different 3D scans of the body. For each of these sets of 3D volume data, the above-mentioned processing (segmentation, slice generation and evaluation) is performed by the ultrasound system 10. The plurality of sets of volume data resulting from the different 3D scans and the 2D slices that are generated in the above-mentioned way from said sets of volume data may be stored within the memory (MEM) 36 together with the evaluated quality factors of each of the 2D slices.

In this case a selector (SEL) 44 is configured to select for each 2D standard view a 2D slice that has the highest quality factor. This may be done by comparing the evaluated quality factors of corresponding 2D slices that are generated from each of the plurality of 3D sets of volume data which are stored in the memory 36. In other words, the selector 44 selects for each standard view the best 2D slice out of all 2D slices that have been generated from the different sets of 3D volume data (different ultrasound scans). This means that the different 2D standard views that are simultaneously illustrated on the display 18 may result from different 3D ultrasound scans, wherein the selector 44 automatically determines from which 3D volume data set a specific 2D standard view may be generated best.

This will be explained in the following in further detail by example of a transesophageal echocardiography (TEE).

Figure 3:
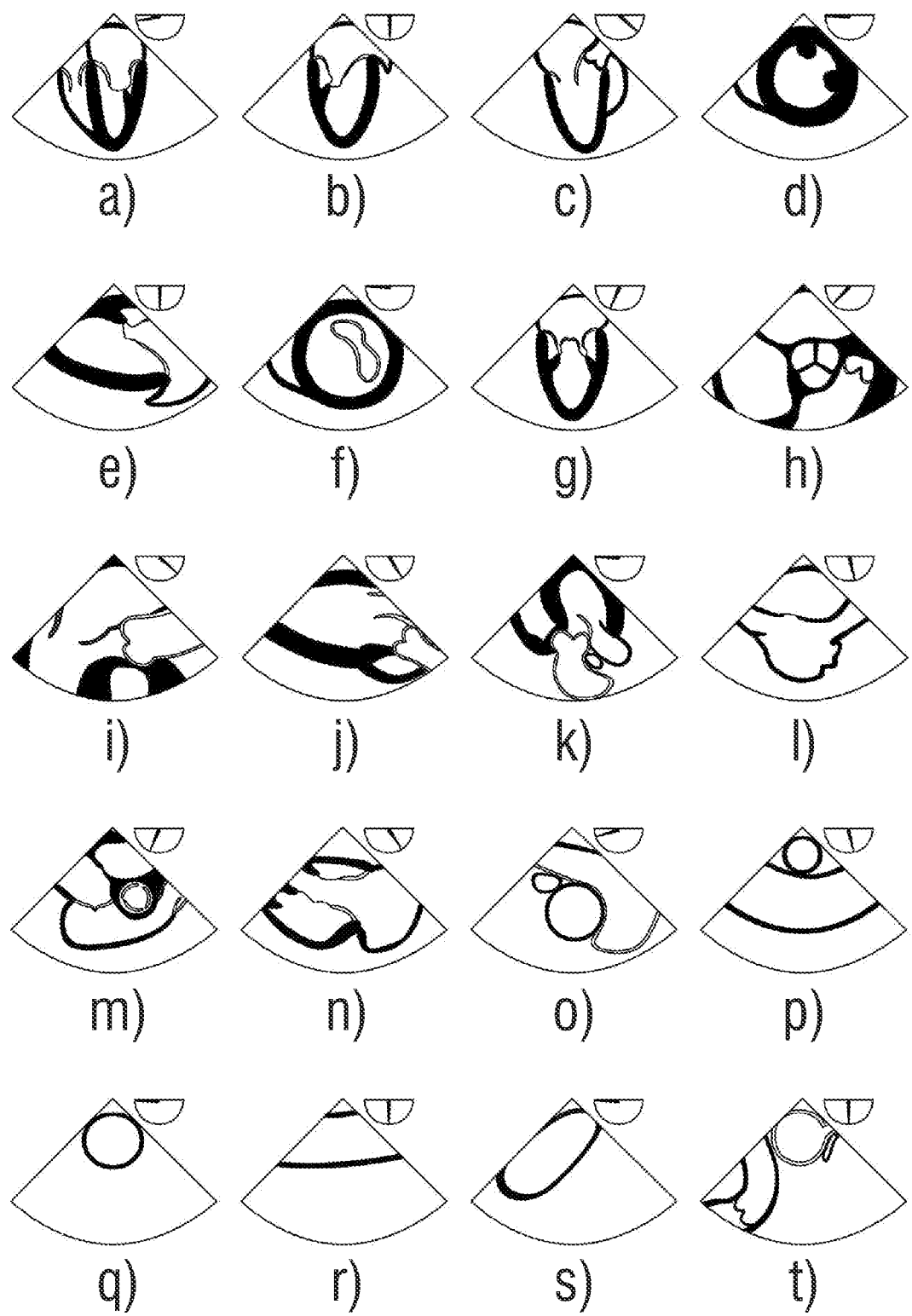
FIG. 3 schematically shows an overview of different 2D standard views of a transesophageal echography (TEE)

For a full TEE examination, 20 different 2D TEE standard views have to be acquired. An overview of the different standard views is given in schematical manner in FIG. 3. FIG. 3a e.g. illustrates the ME four chamber view, FIG. 3b the ME two chamber view, FIG. 3c the ME LAX view and so on.

Figure 4:
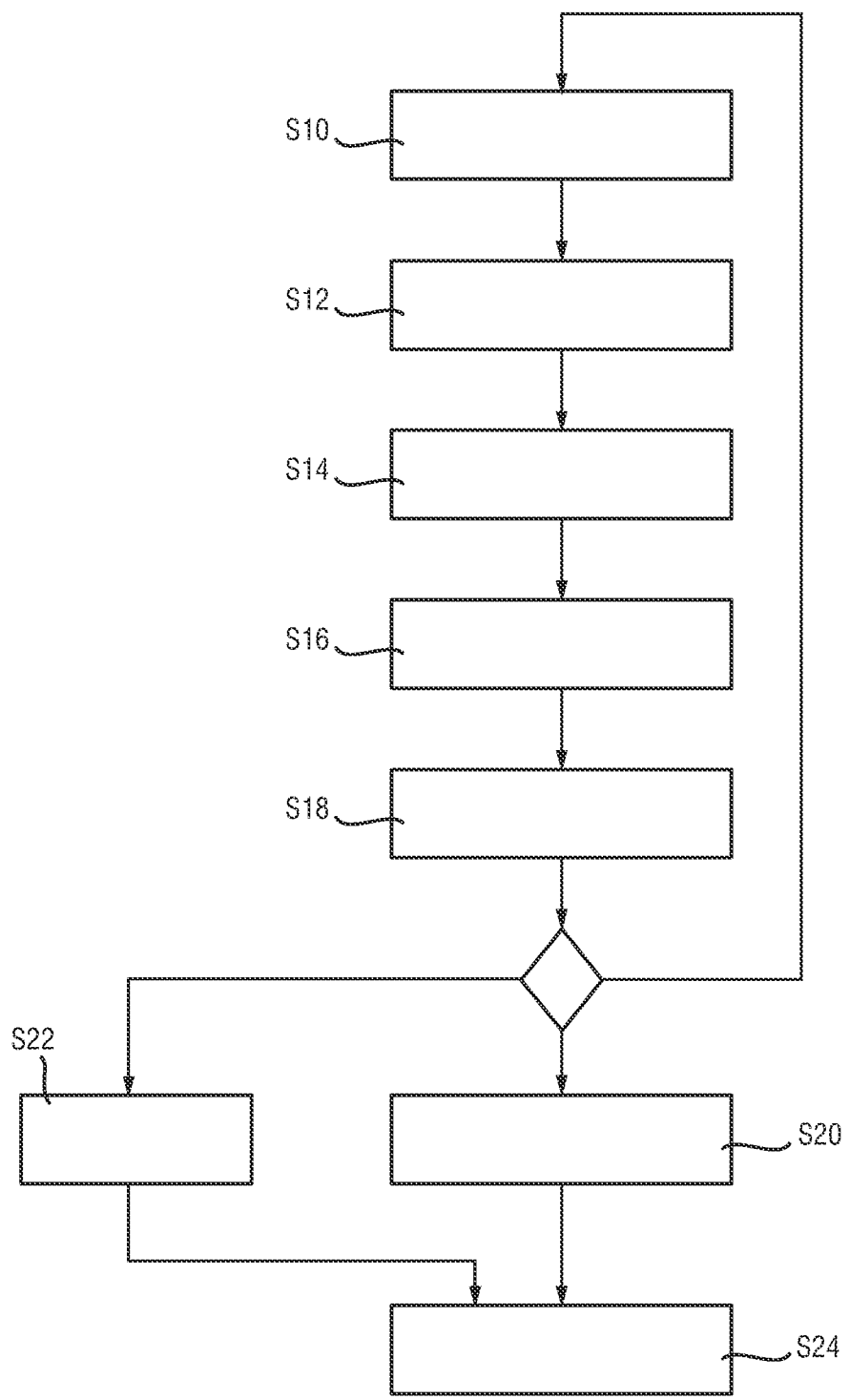
FIG. 4 shows a flow diagram to illustrate an embodiment of the method according to the present invention.

FIG. 4 shows a schematic block diagram for illustrating the method according to an embodiment of the present invention. In a first step S10 a set of volume data resulting from a 3D ultrasound scan of a body is received. In the following step S12 a position and orientation of an anatomical object of interest (e.g. the human heart) is detected within the at least one set of volume data. Thereto, a model-based segmentation of the at least one set of volume data may be conducted. As already mentioned above, this is done by finding a best match between the at least one set of volume data and a geometrical model of the human heart.

Then, said model is used to compute the planes of all 20 TEE standard views. This is done in step S14 by generating a plurality of 2D slices from the at least one set of 3D volume data. Thereto, the respective slice locations are defined based on the geometrical model of the heart. Due to the segmentation that has been performed in advance (in step S12), these respective slice locations may be mapped onto the 3D volume data, such that it is possible to compute the 2D slices from the 3D volume data set by interpolating the 3D image. For example to compute the ME four chamber view (see FIG. 3a), the plane is given by the center of the mitral valve, the center of the tricuspid valve and the apex.

Then, in step S16 it is defined for each 2D standard view which anatomical features of the heart are expected to be contained in said standard view. This may be done by encoding the geometrical model with an anatomy-related description that identifies segments of the heart within each 2D standard view that correspond to respective anatomic features, for example, the heart chambers, the main vessels, the septa, the heart valves, etc. If the geometrical model is encoded with this anatomy-related information, it is easier in the further procedure to evaluate whether the generated 2D slices cover all information that should be included within the respective 2D standard view.

In step S18 it is then evaluated for each of the generated 2D slices how good the 2D standard view is covered. Thereto, a quality factor is computed for each of the generated 2D slices, wherein said quality factor may be a quantitative factor that includes a ratio to which extent the expected anatomical features are included in the respective 2D slice. This may be done by comparing the field of view of each of the generated 2D slices to the geometrical model of the heart.

Figure 5:
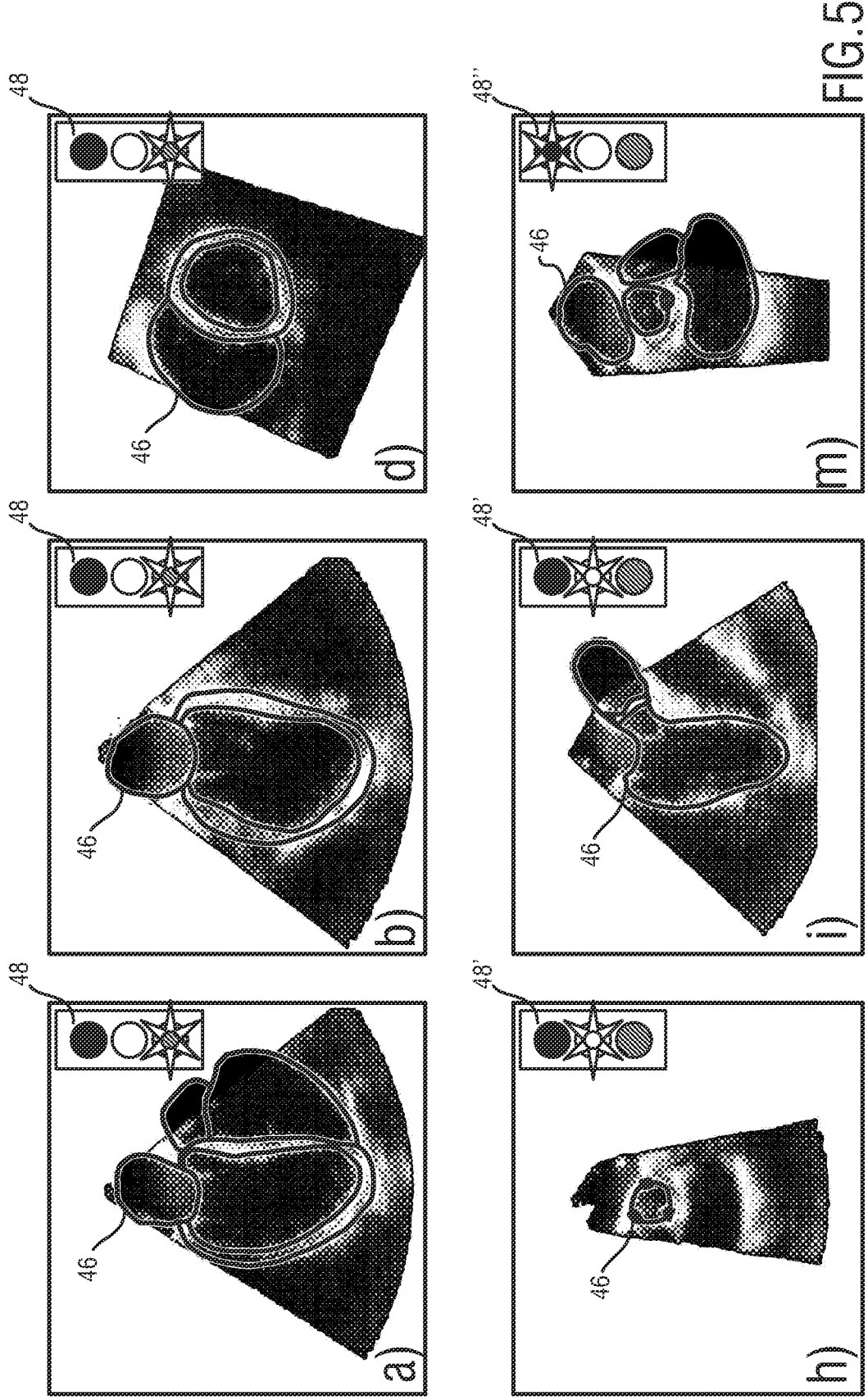
FIG. 5 shows a first exemplary illustration of results received with the ultrasound imaging system.

FIG. 5 shows six 2D slices that have been generated in the above-mentioned way based on a single 3D TEE image (herein referred to as a single set of volume data). The results of the performed segmentation are therein illustrated by border lines 46. FIG. 5a shows the 2D slice that corresponds to the ME four chamber standard view (compare to FIG. 3a). FIG. 5B therein shows the 2D slice that corresponds to the ME two chamber standard view (compare to FIG. 3b). FIG. 3d shows the generated 2D slice that corresponds to the TE mid SAX standard view (compare to FIG. 3d). FIG. 5h shows the generated 2D slice that corresponds to the ME AV SAX standard view (compare to FIG. 3h). FIG. 5i shows the generated 2D slice that corresponds to the ME AV LAX standard view (compare to FIG. 3i). And FIG. 5m shows the generated 2D slice that corresponds to the ME RV inflow-outflow standard view (compare to FIG. 3m).

As it may be seen, most of the anatomical features of interest are within the slices 5a, b and d, i.e. most of the border lines 46 are within the field of view. The quality factors that have been evaluated for these slices are therefore comparatively high, which is indicated in FIG. 5a, b and d by means of a graphical icon 48 that is illustrated in the upper right corner of each slice image and represents a schematical traffic light showing a green light.

It may be furthermore seen that the generated slices 5h and i are still acceptable, because the main anatomical features of interest, e.g. the aortic valve within FIG. 5h, is still within the field of view. The traffic light 48' therefore shows a yellow light for these slices. In FIG. 5m most of the border lines 46 are however out of the field of view, meaning that the anatomical features of interest, i.e. the in and outflow of the right ventricle, are not fully covered. The quality of this generated 2D slice is thus evaluated to be rather low, which is indicated in FIG. 5m with a traffic light 48" that shows a red light.

Returning back to FIG. 4 now, the method steps S10-S18 are repeated for every new 3D TEE image. This means that for every 3D TEE image (every 3D volume data set), all 20 2D slices are generated and evaluated that correspond to the 20 different 2D TEE standard views illustrated in FIG. 3. For every 2D slice it is defined, which anatomical features are to be expected therein, i.e. which border lines 46 should occur in these 2D slices (step S16). And for every 2D slice it is evaluated, whether the expected border lines are within the field of view, or to which extend this is the case (step S18).

Figure 6:
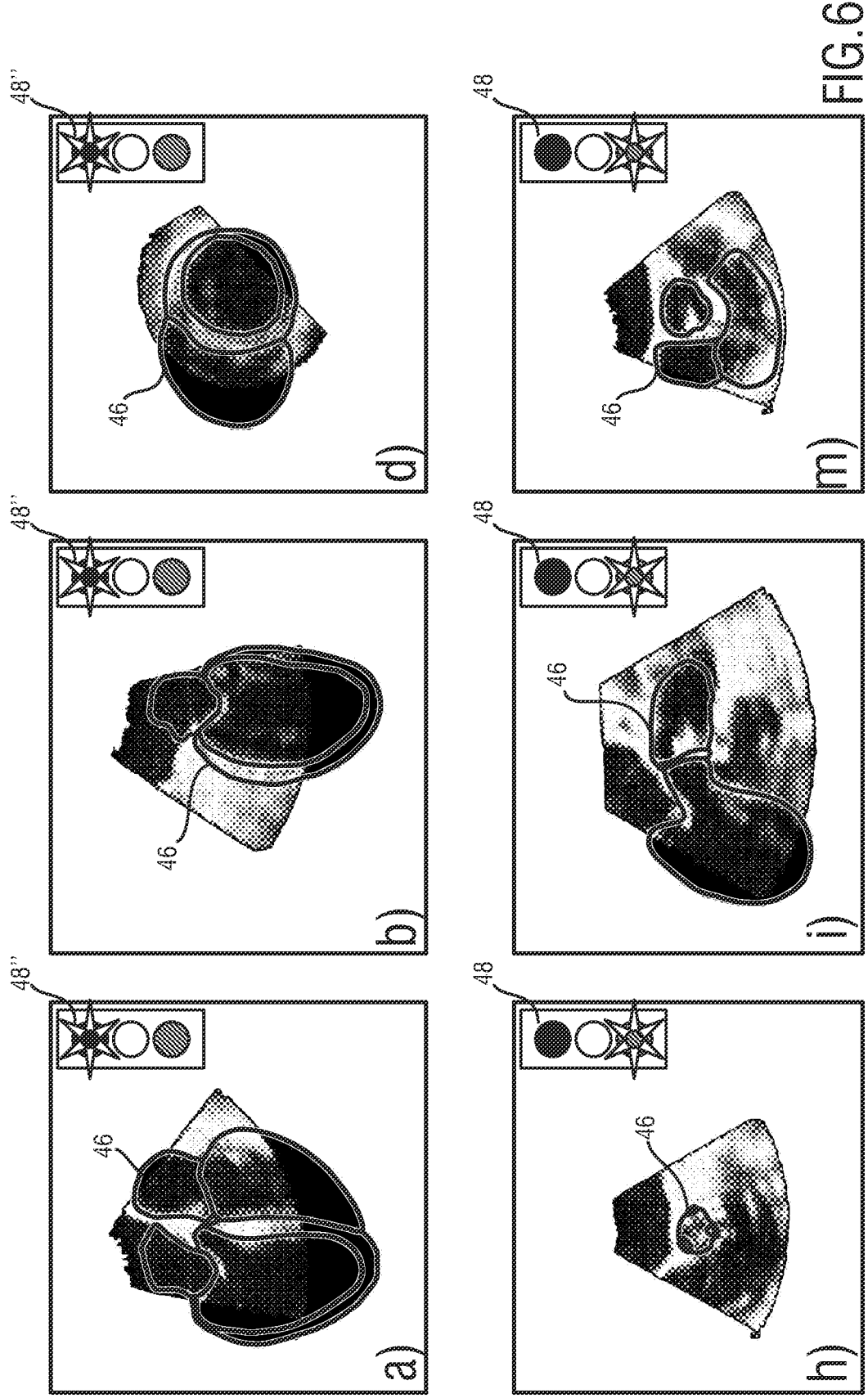
FIG. 6 shows a second exemplary illustration of results received with the ultrasound imaging system.

FIG. 6 illustrates 2D slices that have been generated (and evaluated) based on a second 3D TEE image (second set of volume data) with a different field of view. From FIG. 6 it may be seen that the generated slices 6a, b and d are compared to the slices shown in FIG. 5a, b and d rather unsuitable (indicated by red traffic light 48"). However, the generated 2D slices corresponding to the ME AV SAX standard view (FIG. 6h), the ME AV LAX standard view (FIG. 6i) and to the ME RV inflow-outflow standard view (see FIG. 6m) have a rather good quality, since the anatomical features of interest (border lines 46) are this time within the field of view.

It may therefore be seen that the 2D standard views a, b and d are best covered within the 2D slices that were generated from the first 3D volume data set (illustrated in FIG. 5a, b and d), while the 2D standard views h, i and m are best covered within the 2D slices that were generated from the second 3D volume data set (illustrated in FIG. 6h, i and m).

In step S20 (see FIG. 4) the best version for each 2D standard view is then automatically selected. For each 2D standard view one generated 2D slice is selected that has the highest quality factor. This may be done by comparing the evaluated quality factors of corresponding 2D slices generated from each of the received sets of volume data (from each of the received 3D TEE images). This "best selection" is finally illustrated on the display in step S24.

Figure 7:
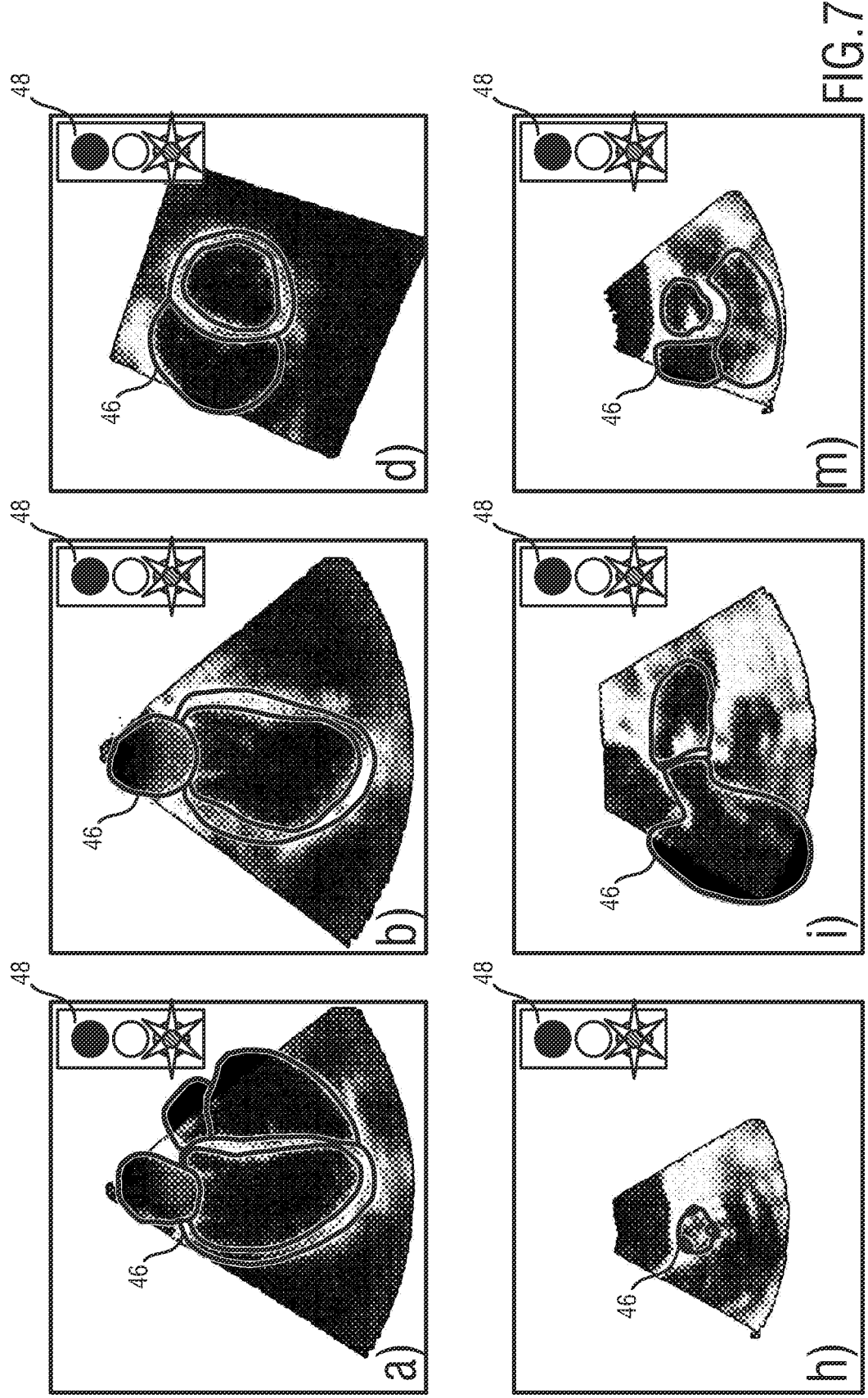
FIG. 7 shows a third exemplary illustration of results received with the ultrasound imaging system.

The result is shown in FIG. 7. As it may be seen in FIG. 7, the system 10 automatically selected the more suitable 2D slices that were generated from the first 3D TEE image as 2D standard views a, b and d, while it automatically selected the 2D slices that were generated from the second 3D TEE image as 2D standard views h, i and m. In summary, this means that only two 3D TEE images were necessary in this example to generate the exemplarily shown six 2D standard views, whereas six different ultrasound scans would be required when manually scanning the patient with a regular 2D ultrasound scanning system. The further significant advantage is that the system selects the best 2D slices by itself. The presented method is thus less error-prone and faster compared to the conventional TEE procedure.

A still further improvement of the method schematically illustrated in FIG. 4 is shown by step S22. Instead of using the 2D slices that were interpolated from the 3D volume data set, the 2D slices may also be generated by performing an additional 2D scan as soon as the system recognizes that a quality factor of a 2D slice that is generated in steps S10-S18 is above a predetermined threshold value. This means that as soon as the system recognizes that the field of view of the taken 3D image is suitable for a specific 2D standard view, the imaging parameters for this 2D standard view from the current location of the transducer probe 14 are computed and the transducer probe 14 automatically performs an additional 2D scan to directly receive the 2D standard view. This "extra" acquisition should however only be done if it has been found in step S18 that the quality of the generated 2D slice is rather high, meaning that the position and orientation of the transducer probe 14 is suitable for acquiring the respective 2D standard view.

It shall be noted that step S22 is not a mandatory, but an optional method step. Of course, a combination of both, generating the 2D slices from the 3D volume data set and generating the 2D slices directly by performing an additional 2D scan, is possible as well.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. An ultrasound imaging system comprising:
one or more processors configured to:
receive first volume ultrasound data of a first scan of an anatomical object within a body obtained by an ultrasound probe positioned at a first position on the body;
receive second volume ultrasound data of a second scan of the anatomical object obtained by the probe positioned at a second position on the body, wherein the second position is different from the first position;
generate, based on the first volume ultrasound data, a first plurality of two-dimensional (2D) ultrasound images, wherein the first plurality of 2D ultrasound images correspond to a set of pre-defined views of the anatomical object, wherein the first plurality of 2D ultrasound images comprises a first ultrasound image corresponding to a first pre-defined view of the set of pre-defined views;
determine a first quality factor of the first ultrasound image;
generate, based on the second volume ultrasound data, a second plurality of 2D ultrasound images corresponding to the set of pre-defined views, wherein the second plurality of 2D ultrasound images comprises a second ultrasound image corresponding to the first pre-defined view;
determine a second quality factor for the second ultrasound image;
perform a comparison between the first quality factor and the second quality factor;
select, for the first pre-defined view, the first ultrasound image and not the second ultrasound image based on the comparison; and
output to a display in communication with the one or more processors:
a third plurality of 2D ultrasound images corresponding to the set of pre-defined views, wherein the third plurality comprises the first ultrasound image and not the second ultrasound image; and
a graphical representation of the first quality factor comprising an icon selected from a plurality of icons, wherein the plurality of icons comprises:
a first icon representative of the first quality factor being within a first range of values; or
a second icon representative of the first quality factor being within a second range of values.

2. The ultrasound imaging system of claim 1, wherein the one or more processors are configured to:
select the first ultrasound image and not the second ultrasound image based on the comparison indicating that the first quality factor is greater than the second quality factor.

3. The ultrasound imaging system of claim 1, wherein, to determine the first quality factor, the one or more processors are configured to compare the first ultrasound image and the first pre-defined view.

4. The ultrasound imaging system of claim 3, wherein the one or more processors are configured to compare a field of view of the first ultrasound image and a feature of the anatomical object associated with the first pre-defined view.

5. The ultrasound imaging system of claim 4, wherein the one or more processors are configured to determine an amount of overlap between the field of view and the feature.

6. The ultrasound imaging system of claim 3, wherein the one or more processors are configured to compare the first ultrasound image and a geometrical model comprising the first pre-defined view.

7. The ultrasound imaging system of claim 1, wherein the graphical representation of the first quality factor comprises a percentage.

8. The ultrasound imaging system of claim 1, wherein the plurality of icons further comprises a third icon representative of the first quality factor being within a third range of values.

9. The ultrasound imaging system of claim 8, wherein at least one of the first icon, the second icon, or the third icon is configured to indicate that a user obtain additional volume ultrasound data of the anatomical object.

10. The ultrasound imaging system of claim 1, wherein the one or more processors are configured to output the third plurality such that each 2D ultrasound image of the third plurality is displayed simultaneously.

11. The ultrasound imaging system of claim 1, further comprising the display.

12. The ultrasound imaging system of claim 1, further comprising the ultrasound probe.

13. The ultrasound imaging system of claim 1,
wherein the first volume ultrasound data comprises a first single 3D ultrasound image, and
wherein the second volume ultrasound data comprises a second single 3D ultrasound image.

14. The ultrasound imaging system of claim 13,
wherein the first ultrasound image comprises a first slice of the first single 3D ultrasound image, and
wherein the second ultrasound image comprises a second slice of the second single 3D ultrasound image.

15. The ultrasound imaging system of claim 1,
wherein the first volume ultrasound data is obtained by the ultrasound probe in a first orientation on the body,
wherein the second volume ultrasound data is obtained by the ultrasound probe in a second orientation on the body, and
wherein the second orientation is different from the first orientation.

16. The ultrasound imaging system of claim 1,
wherein the one or more processors are configured to select a third ultrasound image from the second plurality that corresponds to a second pre-defined view of the set of pre-defined views, and
wherein the third plurality of 2D ultrasound images comprises the third ultrasound image.

17. An ultrasound imaging system comprising:
one or more processors configured to:
receive first volume ultrasound data of a first ultrasound scan of an anatomical object within a body obtained by an ultrasound probe positioned at a first position on the body;
receive second volume ultrasound data of a second ultrasound scan of the anatomical object obtained by the ultrasound probe positioned at a second position on the body, wherein the second position is different from the first position;
generate, based on the first volume ultrasound data, a first plurality of two-dimensional (2D) ultrasound images, wherein the first plurality of 2D ultrasound images correspond to a set of pre-defined views of the anatomical object, wherein the first plurality of 2D ultrasound images comprises a first ultrasound image corresponding to a first pre-defined view of the set of pre-defined views;

perform a first comparison between a field of view of the first ultrasound image and a feature of the anatomical object associated with the first pre-defined view, wherein the first comparison comprises a determination of an amount of overlap between the field of view and the feature;

determine a first quality factor of the first ultrasound image based on the first comparison;

generate, based on the second volume ultrasound data, a second plurality of 2D ultrasound images corresponding to the set of pre-defined views, wherein the second plurality of 2D ultrasound images comprises a second ultrasound image corresponding to the first pre-defined view;

determine a second quality factor for the second ultrasound image;

perform a second comparison between the first quality factor and the second quality factor;

select, for the first pre-defined view, the first ultrasound image and not the second ultrasound image based on the second comparison; and output, to a display in communication with the one or more processors, a third plurality of 2D ultrasound images corresponding to the set of pre-defined views, wherein the third plurality comprises the first ultrasound image and not the second ultrasound image.

18. The ultrasound imaging system of claim 17, wherein the one or more processors are configured to select a third ultrasound image from the second plurality that corresponds to a second pre-defined view of the set of pre-defined views, and wherein the third plurality of 2D ultrasound images comprises the third ultrasound image.

19. The ultrasound imaging system of claim 17, wherein the one or more processors are configured to:

select the first ultrasound image and not the second ultrasound image based on the second comparison indicating that the first quality factor is greater than the second quality factor.

20. The ultrasound imaging system of claim 17, wherein the one or more processors are configured to output a graphical representation of the first quality factor to the display.

* * * * *